United States Patent
Cha et al.

(10) Patent No.: US 11,215,547 B2
(45) Date of Patent: Jan. 4, 2022

(54) METHOD OF EVALUATING GAS PERMEABILITY OF POLYMER MEMBRANE BASED ON MOLECULAR DYNAMICS SIMULATION

(71) Applicants: Hyundai Motor Company, Seoul (KR); Kia Motors Corporation, Seoul (KR)

(72) Inventors: Jin Hyeok Cha, Gyeonggi-do (KR); Woong Pyo Hong, Gyeonggi-do (KR); Suk Hwan Yun, Gyeonggi-do (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 63 days.

(21) Appl. No.: 16/692,812

(22) Filed: Nov. 22, 2019

(65) Prior Publication Data
US 2020/0340906 A1    Oct. 29, 2020

(51) Int. Cl.
| | | |
|---|---|---|
| *G01N 15/08* | (2006.01) | |
| *G16C 10/00* | (2019.01) | |
| *G06F 30/00* | (2020.01) | |
| *H01M 50/411* | (2021.01) | |

(52) U.S. Cl.
CPC ....... *G01N 15/08* (2013.01); *G01N 2015/086* (2013.01); *G06F 30/00* (2020.01); *G16C 10/00* (2019.02); *H01M 50/411* (2021.01); *H01M 2300/0082* (2013.01)

(58) Field of Classification Search
CPC .. G01N 15/00; G01N 15/08; G01N 2015/086; G06F 30/00; G18C 10/00; H01M 50/411; H01M 2300/0082
See application file for complete search history.

(56) References Cited

U.S. PATENT DOCUMENTS

| | | | | |
|---|---|---|---|---|
| 7,815,859 B2 * | 10/2010 | Kennedy | ............ | G01N 15/0826 422/68.1 |
| 7,846,981 B2 * | 12/2010 | Lee | ............... | H01M 8/1058 521/27 |
| 9,200,996 B2 * | 12/2015 | AlSofi | ............... | G01N 15/0826 |
| 10,161,846 B2 * | 12/2018 | Brule | ................ | G01N 15/082 |
| 2017/0336315 A1 * | 11/2017 | Kim | ................ | G01N 27/3335 |
| 2020/0056976 A1 * | 2/2020 | Kim | ................ | G06F 17/10 |

* cited by examiner

*Primary Examiner* — Nguyen Q. Ha
(74) *Attorney, Agent, or Firm* — Mintz Levin Cohn Ferris Glovsky and Popeo, P.C.; Peter F. Corless

(57) ABSTRACT

The present invention provides a method for measuring gas permeability of a polymer membrane, for example, by evaluating polymer-structure influence on gas permeability in of a polymer membrane.

15 Claims, 12 Drawing Sheets

(2) 2layer polymer membrane (3) 3layer polymer membrane (4) 4layer polymer membrane (5) 5layer polymer membrane w/short side chain    w/long side chain

METHOD OF EVALUATING GAS PERMEABILITY OF POLYMER MEMBRANE BASED ON MOLECULAR DYNAMICS SIMULATION

CROSS-REFERENCE TO RELATED APPLICATION

This application claims under 35 U.S.C. § 119(a) the benefit of priority to Korean Patent Application No. 10-2019-0048465 filed on Apr. 25, 2019, the entire contents of which are incorporated herein by reference.

TECHNICAL FIELD

The present invention relates to a method for evaluating the gas permeability of a polymer membrane, for example, by evaluating polymer-structure influence on gas permeability of a polymer membrane.

BACKGROUND

The permeability of polymer membranes may be one of the major factors in determining the properties of polymer membranes, including durability and conductivity. For example, in the case of a polymer electrolyte membrane in which ion migration occurs, the change of the permeability is very important because it is directly related to the performance efficiency.

The gas permeability can be measured experimentally, but it takes a lot of time and money to evaluate gas permeability dependence on the molecular structure of polymer membranes.

In particular, since gases vary greatly in size depending on their types, it is very difficult to evaluate the influence of the structural change of the molecular unit or the kind of constituent atoms.

In other words, it can be seen from the results whether molecules of a certain structure are ultimately effective in controlling gas permeability, but it is difficult to precisely control the gas permeability based on the mechanism.

Meanwhile, in recent years, the application of molecular dynamics simulation has been widely expanded due to the rapid development of computer performance and the development of parallel programming techniques, such as by using of molecular dynamics modeling, a computer modeling technique, has made it possible to quantitatively predict the various properties of macromolecules such as polymers. Studies on the gas permeability depending on the polymer structure are also possible through molecular dynamics simulation, but there are some problems in many modeling calculations that have been reported so far.

Typically, it is difficult to clearly express molecular structure dependence. For example, a polymer has a very complex structure, and a polymer membrane is not formed of a single polymer chain, but is formed of a plurality of entangled polymer chains, and hence it is not easy to conclude what permeability is influenced by only one molecular structure and to identify its mechanism.

In addition, when measuring the permeability of a membrane through molecular dynamics simulations, it is impossible to supply gas to one side of a membrane placed in the center and measure the permeability at the other side of the membrane, because it is like realizing infinite space. Therefore, many researchers indirectly evaluate the permeability based on mean square displacement (MSD), which indicates how far the particles in an already prepared polymer membrane migrated from the initial position. Although this is sufficient to show the gas permeability or particle behavior of the prepared polymer membrane, it is difficult to express the influence of a single pure polymer chain structure on the permeability, because it includes all of the infinite influential factors (such as the structural changes made from adjacent chains and the various free-moving spaces resulting therefrom) that occur during the formation of the polymer membrane.

The above information disclosed in this Background section is only for enhancement of understanding of the background of the invention and therefore it can contain information that does not form the prior art that is already known in this country to a person of ordinary skill in the art.

SUMMARY

In preferred aspects, provided is a method for determining a mechanism of a relationship (e.g., interactions) between the molecular structure and gas permeability of a polymer membrane.

Further provided is a method which may minimize infinite influential factors that influence gas permeability of a gas-permeable polymer membrane by quantitatively evaluating the influence of a single polymer chain of the gas-permeable polymer membrane on the gas permeability.

The objects of the present invention are not limited to the objects described above. The objects of the present invention will be more apparent from the description below and implemented by means described in the claims and a combination thereof.

In one aspect, the present invention provides a method of measuring the gas permeability of a polymer membrane. The method may include the steps of: providing a polymer unit cell to be measured for its permeability; adjusting a volume of the polymer unit cell; providing or adding or permeating a permeating gas that permeates through the polymer unit cell; and allowing or supplying the permeating gas to permeate through the polymer unit cell and measuring a relative concentration of the permeating gas. Preferably, the polymer unit cell may be cubic in shape, and the cubic polymer unit cell may include a single polymer chain.

The step of providing the polymer unit cell may include the steps of: providing a main chain of the polymer chain; and providing a side chain of the polymer chain such as by reaction of the polymer main chain to provide a polymer with side chain, or the main side with side chain may be synthesized together such as by reaction of appropriate monomers or oligomers.

In the step of providing the main chain of the polymer chain, a length of the main chain may be adjusted, such as during the synthesis of the main chain of the polymer.

In the step of providing the side chain of the polymer chain, a length of the side chain or a number of side chains connected to the main chain may be adjusted.

The polymer chain may suitably include a polymer including a modified or unmodified fluoropolymer-copolymer. Preferably, the polymer chain may include a sulfonated tetrafluoroethylene based fluoropolymer-copolymer, such as Nafion.

The polymer unit cell may further include a cation and water.

The single polymer chain included in the polymer unit cell may spontaneously rotate or twist to change its shape toward higher entropy.

Alternatively, the single polymer chain included in the polymer unit cell may be changed into two or more shapes.

In the step of adjusting the volume of the polymer unit cell, the volume of the polymer unit cell may be adjusted in a decreasing direction.

Alternatively, the step of adjusting the volume of the polymer unit cell, the density of the polymer chain included in the polymer unit cell may be adjusted in an increasing direction.

A number of the polymer unit cell may be two or more, and after the step of adjusting the volume of the polymer unit cell, the two or more polymer unit cells may be stacked in one direction.

Preferably, the two or more polymer unit cells may be stacked in a direction in which the permeating gas permeates through the polymer unit cell.

The two or more polymer unit cells may be stacked into at least four layers.

In the step of evaluating the relative concentration of the permeating gas, the permeating gas may permeate in only one direction when the permeating gas permeates through the polymer unit cell.

In the step of evaluating the relative concentration of the permeating gas, the relative concentration of the permeating gas may be measured in only one polymer unit cell, which first contacts the permeating gas, among the two or more stacked polymer unit cells.

The above and other features of the invention are discussed infra.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

Figure 1:
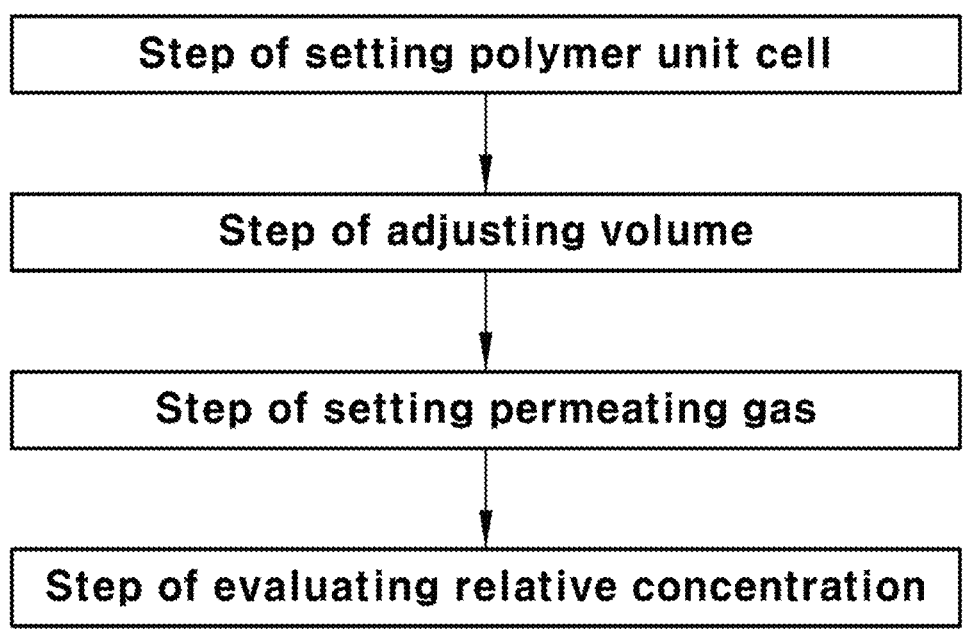
FIG. 1 is a flow chart illustrating an exemplary method of evaluating the gas permeability of an exemplary polymer membrane according to an exemplary embodiment of the present invention.

It should be understood that the appended drawings are not necessarily to scale, presenting a somewhat simplified representation of various exemplary features illustrative of the basic principles of the invention. The specific design features of the present invention as disclosed herein, including, for example, specific dimensions, orientations, locations, and shapes will be determined in section by the particular intended application and use environment.

In the drawings, reference numbers refer to the same or equivalent sections of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The above objects, other objects, features, and advantages of the present invention will be easily understood through the following preferred exemplary embodiments with reference to the accompanying drawings. The present invention is not limited to the embodiments described therein and may also be modified in various different ways. On the contrary, embodiments introduced herein are provided to make disclosed contents thorough and complete and sufficiently transfer the spirit of the present invention to those skilled in the art.

In the description of each drawing, like reference numerals are used for like constitute elements. In the accompanying drawings, dimensions of structures are illustrated to be more enlarged than actual dimensions for clarity of the present invention. Terms such as first, second, and the like may be used to describe various components and the components should not be limited by the terms. The terms are used to only distinguish one component from another component. For example, a first component may be referred to as a second component, and similarly, the second component may be referred to as the first component without departing from the scope of the present invention. Singular expressions used herein include plurals expressions unless they have definitely opposite meanings in this context.

In the present specification, it should be understood that the term "include" or "have" indicates that the feature, number, step, operation, component, part, or combination thereof described in the specification is present, but does not exclude a possibility of presence or addition of one or more other features, numbers, steps, operations, components, parts or combinations thereof, in advance. In addition, it will be understood that when an element such as a layer, film, region, or plate is referred to as being "on" another element, it can be "directly on" the other element or intervening elements may also be present. On the contrary, it will be understood that when an element such as a layer, film, region, or plate is referred to as being "below" another element, it can be "directly below" the other element or intervening elements may also be present.

Unless otherwise indicated, all numbers, values and/or expressions referring to quantities of ingredients, reaction conditions, polymer compositions, and formulations used herein are to be understood as modified in all instances by the term "about" as such numbers are inherently approximations that are reflective of, among other things, the various uncertainties of measurement encountered in obtaining such values. Further, where a numerical range is disclosed herein, this range is continuous, and includes unless otherwise indicated, every value from the minimum value to and including the maximum value of such a range. Still further, where such a range refers to integers, unless otherwise indicated, every integer from the minimum value to and including the maximum value is included.

In the context of this specification, where a range is stated for a parameter, it will be understood that the parameter includes all values within the stated range, inclusive of the stated endpoints of the range. For example, a range of "5 to 10" will be understood to include the values 5, 6, 7, 8, 9, and 10 as well as any sub-range within the stated range, such as to include the sub-range of 6 to 10, 7 to 10, 6 to 9, 7 to 9, etc., and inclusive of any value and range between the integers which is reasonable in the context of the range stated, such as 5.5, 6.5, 7.5, 5.5 to 8.5 and 6.5 to 9, etc. Further, for example, a range of "10% to 30%" will be understood to include the values 10%, 11%, 12%, 13%, etc., and all integers up to and including 30%, as well as any sub-range within the stated range, such as to include the sub-range of 10% to 15%, 12% to 18%, 20% to 30%, etc., and inclusive of any value and range between the integers which is reasonable in the context of the range stated, such as 10.5%, 15.5%, 25.5%, etc.

The present invention relates to a method of measuring (e.g., evaluating) the gas permeability of a polymer membrane based on molecular dynamics simulation, which can save time and budget compared to a conventional art by performing simple measurement through computer-based simulation without experimentally evaluating the gas permeability of the polymer membrane. Particularly, the present invention relates to a method for measuring the gas permeability of a polymer membrane, which may include the steps of: providing a polymer unit cell to be measured for its permeability; adjusting the volume of the polymer unit cell; providing, adding or permeating a permeating gas that permeates through the polymer unit cell; and allowing or supplying the permeating gas to permeate through the polymer unit cell and measuring the relative concentration of the permeating gas.

A system for measuring permeability according to the present invention includes a computer mainframe, a keyboard and a mouse as input devices, and a monitor as an output device.

The computer mainframe includes a central processing unit (CPU), a mass storage device (ROM, working memory, and magnetic disc), and a CD drive.

Here, the mass storage unit may be a unit storing a program for executing a simulation.

FIG. 1 is a flow chart illustrating an exemplary method of measuring (e.g., evaluating) the gas permeability of a polymer membrane according to an exemplary embodiment of the present invention. With reference to FIG. 1, each step will be described in detail below.

Step of Providing Polymer Unit Cell

This step may include providing a polymer unit cell to be measured for permeability. Particularly, the step may include selecting a polymer chain constituting a material to be evaluated for its permeability and constructing a virtual cell from the polymer chain, thereby providing a polymer unit cell.

The polymer unit cell of the present invention may suitably be cubic in shape and may include a single polymer chain in the virtual space thereof.

The polymer chain is not particularly limited in the present invention, and may vary depending on what kind of polymer membrane to be measured for permeability is selected.

The polymer membrane may suitably include perfluorosulfonic acid (PFSA), or a polymer including a modified or unmodified fluoropolymer-copolymer. Preferably, the polymer chain may include a sulfonated tetrafluoroethylene based fluoropolymer-copolymer, such as Nafion.

Figure 2:
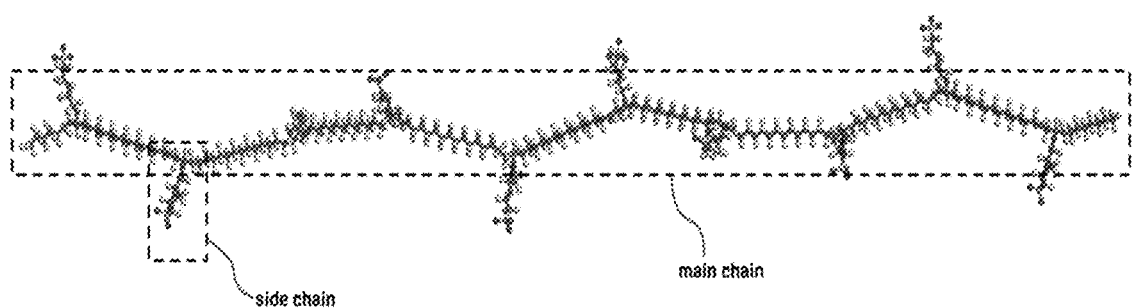
FIG. 2 illustrates an exemplary single polymer chain of the polymer membrane Nafion which is an exemplary embodiment of the present invention.

The polymer chain is a base polymer constituting the polymer membrane to be measured for permeability, and FIG. 2 illustrates the single polymer chain of the polymer membrane Nafion which is an exemplary embodiment of the present invention.

As shown in FIG. 2, the single polymer chain may include a main chain and side chains, for example, Nafion includes: a main chain that forms the longest chain and contains carbon (C) and fluorine (F); and side chains that are connected to the side of the main chain to form a plurality of short chains and contains a sulfonate group at the end. The main chain of Nafion has the repeat unit $CF_2$, and the side chain is connected to one carbon (C) of the $CF_2$ of the main chain.

This step may further include: a step of providing the main chain of the polymer chain, and a step of providing the side chains of the polymer chain.

The main chain may be provided in any of a variety of ways and syntheses including adjusting the length of the main chain, and the side chains may be provided by adjusting the length of the side chains or the number of side chains connected to the main chain through suitable synthetic reaction.

Figure 3A:
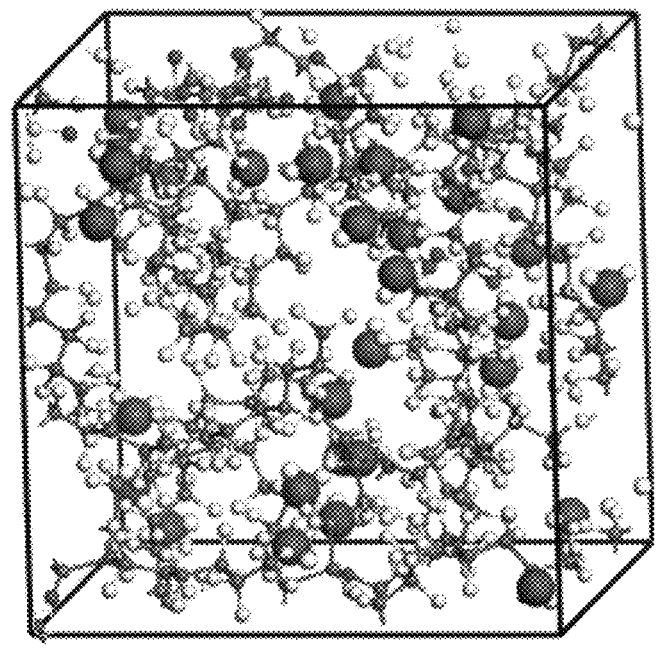
FIG. 3A illustrates an exemplary polymer unit cell including an exemplary single polymer chain (which has a short side chain) of an exemplary polymer membrane Nafion according to an exemplary embodiment of the present invention.
Figure 3B:
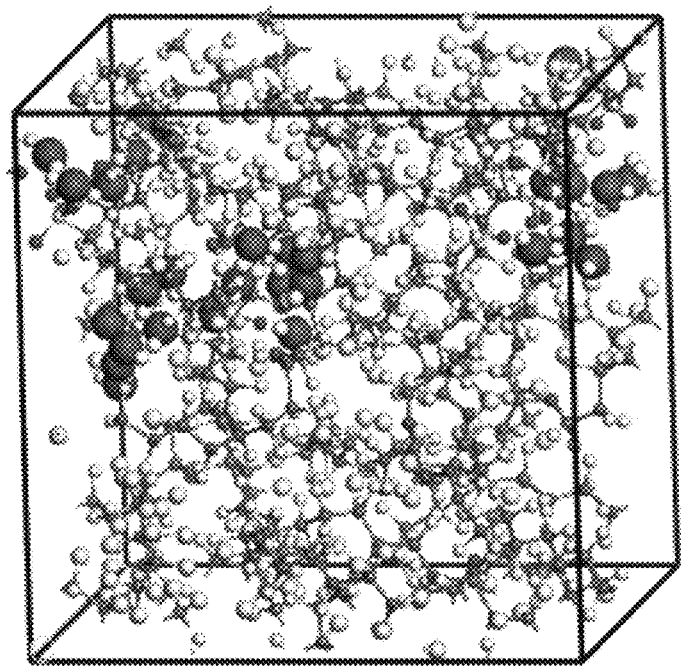
FIG. 3B illustrates an exemplary polymer unit cell including an exemplary single polymer chain (which has a long side chain) of an exemplary polymer membrane Nafion according to an exemplary embodiment of the present invention.

FIG. 3A and FIG. 3B illustrate, respectively, an exemplary polymer unit cell including the single polymer chain of the polymer membrane Nafion according to an exemplary embodiment of the present invention.

The side chain of the polymer chain constituting the Nafion may be an influential factor that plays a critical role in the conduction of ions in the electrolyte membrane. Particularly, the sulfonate group at the side-chain end plays a crucial role in the transport of cations in the electrolyte membrane.

As shown FIG. 3A, it can be seen that the side chain, an influential factor that plays a critical role in the conduction of ions as described above, is a short side chain, and as shown in FIG. 3B, it can be seen that the side chain is a long side chain.

In the present invention, the weight of the polymer chain may be preferably 10 monomers or greater.

The polymer membrane including Nafion may be used as an electrolyte membrane for a battery. In the present invention, the polymer membrane may preferably further include a cation and water to impart the same conditions as those the electrolyte membrane to the polymer membrane.

Step of Adjusting Volume

This step may include adjusting the volume of the polymer unit cell. As described above, the polymer unit cell of the present invention may include a polymer chain in the virtual cubic space, and the polymer chain spontaneously may change its shape under a certain pressure. Particularly, the molecules constituting the polymer chains partially may rotate, so that the main chain and side chains of the polymer chain may change their shape. At this time, the polymer chain twists and changes its shape toward greater entropy (a spontaneous behavior in which the molecular structure of polymer chain goes to the lowest energy state by the atomic interaction force). Void spaces generated due to twisting of the polymer chain as described above may be an influential factor that directly influences the permeability.

The single polymer chain included in the polymer unit cell of the present invention may be changed into two or more shapes, and thus the influence of the structure of the polymer chain on the gas permeability can ultimately be confirmed.

As the polymer chain spontaneously changes its shape, the volume of the virtual polymer unit cell including the polymer chain may also be changed. Preferably, the volume of the polymer unit cell may be adjusted in a decreasing direction under a certain pressure, atomic number and temperature. Namely, it is adjusted in a direction in which the density of the polymer chain included in the polymer unit cell increases.

In the present invention, the density of the polymer unit cell including a single polymer chain preferably may increase until it becomes equal to the density of an actual polymer membrane. That is, the volume decreases to the target density value of the actual polymer membrane while the internal energy is kept at a stable level.

Figure 4A:
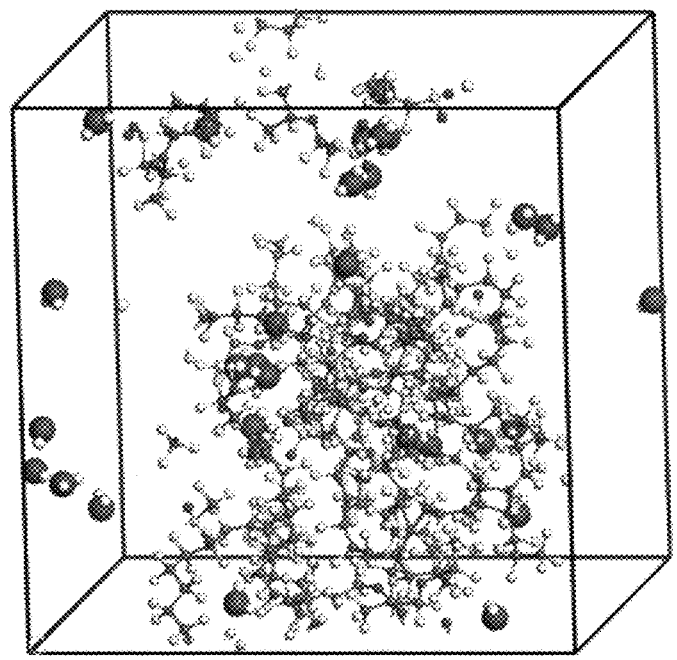
FIG. 4A illustrates that an exemplary polymer chain shape with relatively high structural stress.
Figure 4B:
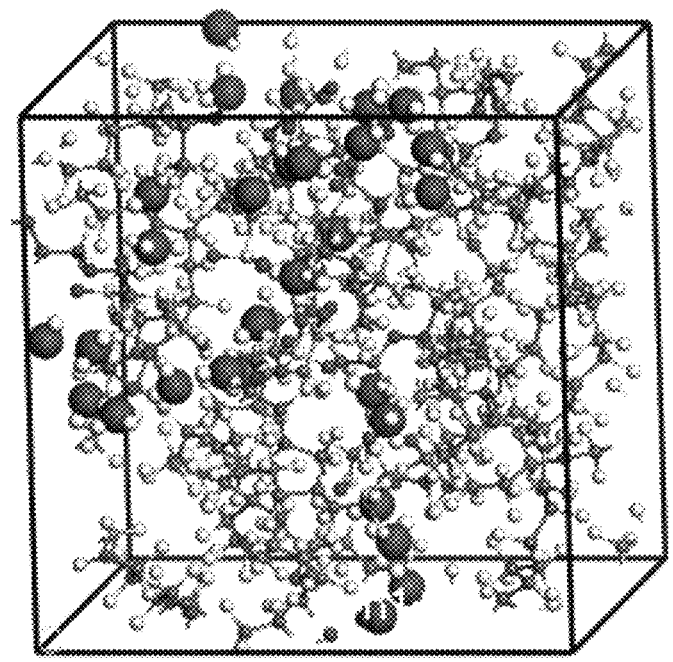
FIG. 4B illustrates that an exemplary polymer chain shape with less structural stress.

FIG. 4A and FIG. 4B illustrate an exemplary embodiment in which that the volume of a polymer unit cell may be changed by the shape change of a polymer chain. As shown in FIG. 4A and FIG. 4B, it can be seen that since a polymer chain has relatively large amounts of a linear main chain and side chains, each linking portion spontaneously may twist, and thus a polymer chain shape with relatively high structural stress (FIG. 4A) may change in to a polymer chain shape with less structural stress (FIG. 4B), and thus the volume of the polymer unit cell including the polymer chain may decrease.

The two or more polymer unit cells including polymer chains may have the same shape. For example, two or more polymer unit cells having the same shape as a result of adjusting their volume may be provided and the two or more polymer unit cells may be stacked in one direction after the step of adjusting the volume of the polymer unit cells. The two or more polymer unit cells may be stacked in only one direction in a three-dimensional xyz-coordinate space. Particularly, the two or more polymer unit cells may be stacked on each other in a direction in which the permeating gas permeates. Preferably, the two or more polymer unit cells may be stacked into at least four layers. In order to obtain more reliable results, these polymer unit cells should preferably be stacked into five or more layers. This is because, when the layer after passing through the first polymer unit cell is thin, the permeating gas that completely passes through the polymer unit cell may flow back to the polymer unit cell due to the technical characteristics of the molecular dynamics simulation, thereby doubly influencing the polymer unit cell.

When two or more polymer unit cells are stacked as described above, the each polymer unit cells may be uniform (the polymer chains in the polymer unit cells have the same structure) so that influence from other influential factors can be minimized.

Figure 5A:
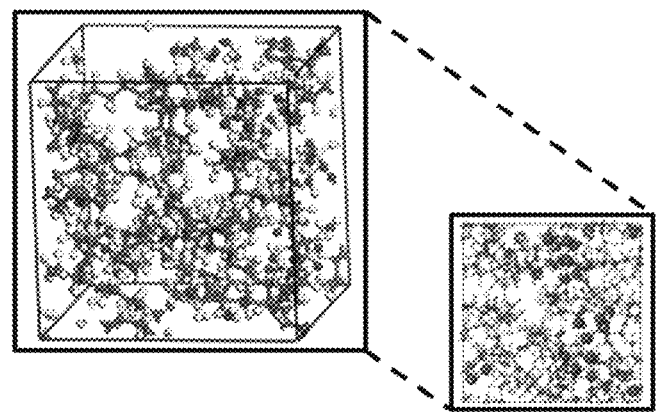
FIG. 5A illustrates an exemplary single polymer unit cell according to an exemplary embodiment of the present invention in two-dimensional planar forms.
Figure 5B:
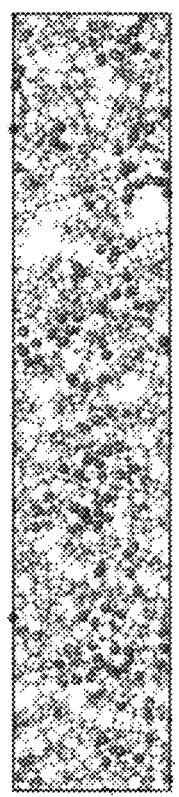
FIG. 5B illustrates a stacked form of exemplary polymer unit cells according to an exemplary embodiment of the present invention in two-dimensional planar forms.

FIG. 5A and FIG. 5B compares a single polymer unit cell (FIG. 5A) of the present invention and a stacked form of polymer unit cells (FIG. 5B) in a two-dimensional planar form. The single polymer unit cell may have a three-dimensional cubic shape, and the stacked form of two or more polymer unit cells may have a three-dimensional rectangular parallelepiped shape.

In general, when a molecular unit simulation is implemented to evaluate the permeability of a material, several polymers are randomly placed in one unit cell to form an evaluation system. Since all the molecules are interlocked in all the axial directions in the xyz coordinate system, the overall influence may be considered, not the influence of the fundamental structure constituting one polymer chain.

In particular, when evaluating the permeability of high-density materials such as Nafion, it is difficult to perform objective evaluation for single polymer chains because the influence on each other is significant. For example, when the gas permeability is evaluated after randomly dispersing polymer chains to make a high density, it is difficult to evaluate the structural influences of the main chain or side chains forming one polymer chain.

In the mechanism of gas permeation through a permeable material, the structural influence of one polymer chain is very important. In particular, in the case of high density materials, the permeability at the interface that meets permeating gas may be absolutely critical.

Generally, when constructing polymer membrane models in all xyz directions and considering the number of atoms constituting the system, the number of atoms to be treated increases exponentially, which causes the problem that the simulation (calculation) time is consumed more.

In particular, when compared with a structure repeated in one direction, it is not easy to confirm the behavior of each of the polymer on the surface and the permeating gas.

For example, it is much more efficient and accurate to measure the permeability of a polymer unit cell having a size of 5×1×1 in the xyz coordinate system than to measure the permeability of a polymer unit cell having a size of 5×5×5.

When an isotropic structure having the same structure in all directions is formed in the process of constructing the system model for obtaining the permeability as described above, the overall influence of various influential factors may be evaluated or measured. When an anisotropic structure with a one-dimensional orientation is formed, it is possible to eliminate diffusion in an unnecessary direction other than the direction in which the gas permeates, and it also possible to change the polymer chain structure of the polymer unit cell having the interface that first contacts the permeating gas and to accurately evaluate or measure the influence of the structure on the permeability while changing the structure.

In addition, sticking the two or more polymer unit cells may be intended to exclude various influential factors that may occur in the process of measuring the permeability based on only one polymer chain.

The influential factors include three factors, such as polymer movement, gas permeation in both directions, and intrinsic density of a polymer membrane, which will be described with reference to FIGS. 6 to 8.

Figure 6:
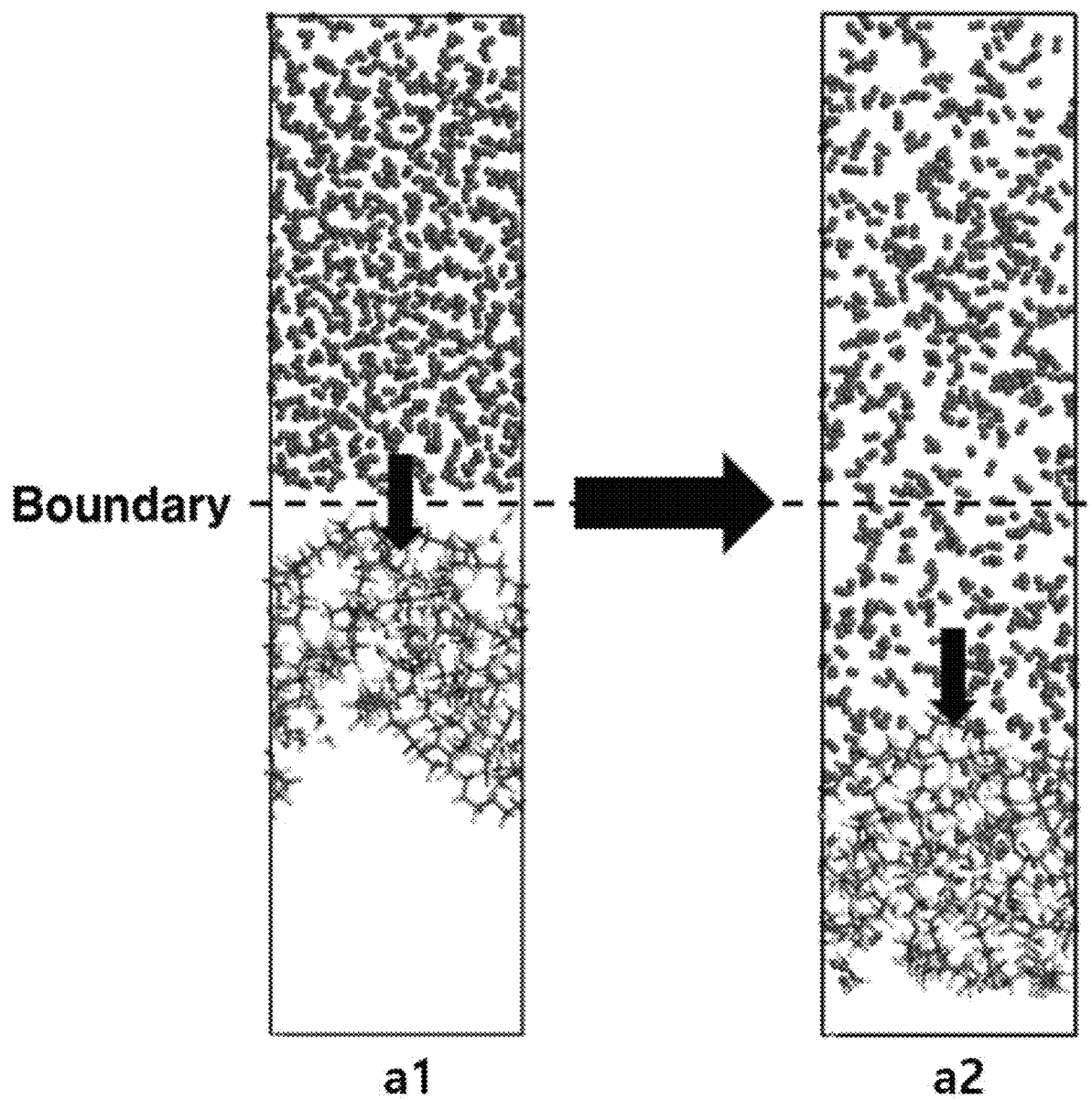
FIG. 6 is a simplified representation of a problem caused by an influential factor (polymer movement) when a single polymer unit cell is applied.

FIG. 6 is related to polymer movement. In order to evaluate the permeability of a polymer membrane, the permeating gas is set to flow in one direction. For example, the permeating gas is supplied to one side of the polymer membrane, and the other side is free of the permeating gas (a1 of FIG. 6). Where an experiment is carried out using only one chain in order investigate how a single polymer chain behaves with respect to the permeation of a permeating gas, the pressures on both sides of the polymer membrane first may be different due to the pressure applied by the permeating gas. When the permeating gas behaves, an external force is applied to the polymer chain by the pressure, and the polymer chain may move in the direction of permeation of the gas (a2 of FIG. 6), and as a result, it may be difficult to reproduce the pure behavior of the polymer membrane depending on the structure.

The basic premise of the molecular dynamics simulation of the present invention with respect to gas permeation in both directions is that there is a periodic boundary condition (PBC). Due to the PBC, permeating gas particles flowing into the polymer membrane occur in both directions of the polymer membrane, and it is difficult to accurately measure the permeating gas particles permeating through the polymer membrane.

Figure 7:
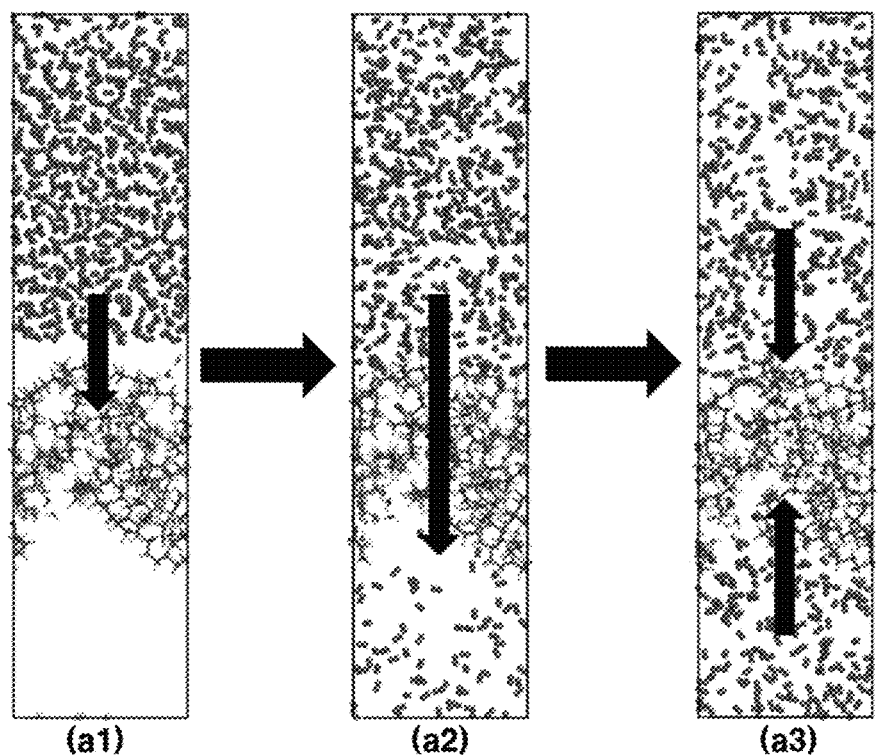
FIG. 7 is a simplified representation of a problem caused by an influential factor (gas permeation in both directions) when a single polymer unit cell is applied.

FIG. 7 shows an example related to this. Particularly, a1 of FIG. 7 shows that the permeating gas permeates through the polymer membrane from one side of the polymer chain under a certain pressure; a2 of FIG. 7 shows that some of the permeating gas particles may move to the opposite side by permeation through the polymer membrane; and a3 of FIG. 7 shows that the permeating gas particles that moved to the opposite side may permeate through the polymer membrane again while applying a certain pressure to the polymer membrane. In other words, it may be difficult to quantitatively evaluate the permeability, due to the mixed permeating gas caused by bi-directional permeation through the polymer chain.

In order to prevent this, in the present invention, polymer unit cells may be repeatedly stacked in one direction (the direction in which the permeating gas permeates), whereby even if the permeating gas particles flow to the opposite side of the polymer membrane, these particles may not influence the statistical treatment of the permeability at the first interface.

Regarding the intrinsic density of the polymer membrane, when the polymer chains constituting the polymer membrane to be measured for permeability are highly dense, the polymer chains tend to twist due to the repulsive force generated therebetween. This is different from the density of the polymer chains used in an actual experiment, and thus it is difficult to consider that the actual density of the polymer chains was realized.

In order to prevent this, in the present invention, polymer unit cells including polymer chains of the same structure at the same density may be repeatedly laminated, thereby suppressing the density change of the polymer chain that first contacts the permeating gas.

Figure 8A:
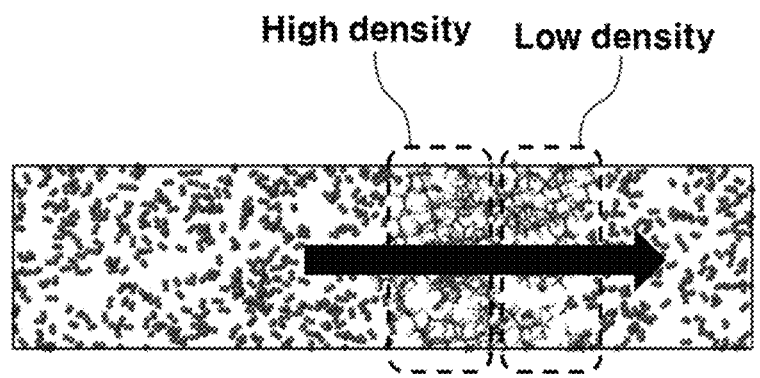
FIG. 8A is a simplified representation of a problem caused by an influential factor (the intrinsic density of a polymer membrane) when a single polymer unit cell is applied.
Figure 8B:
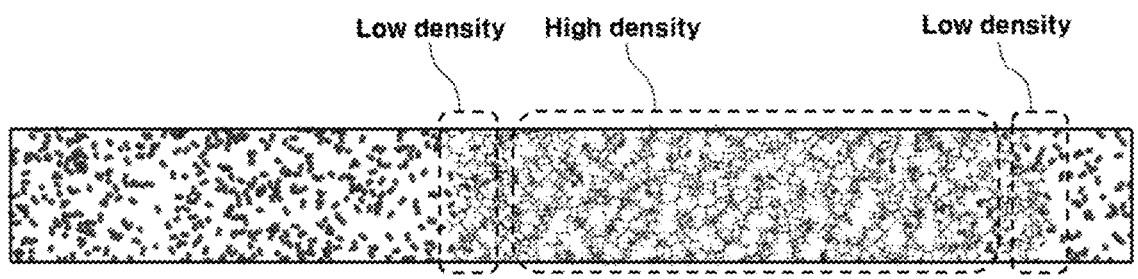
FIG. 8B is a result by an exemplary influential factor (the intrinsic density of a polymer membrane) when a stacked form of exemplary polymer unit cells is applied.

FIG. 8A and FIG. 8B show comparison relating to the intrinsic density of a polymer membrane, which is an influential factor. In the case of FIG. 8A, the structure may be changed due to the force (pressure) by the external permeating gas and the interaction between molecules in the polymer membrane, and eventually, it is divided into two regions: a high-density region and a low-density region.

In the case of FIG. 8B, the structure may be divided into regions by density, similarly to the case of FIG. 8A, and the boundary between the regions may occur. However, since the low-density region is sufficiently thinner than the high-density layer, it may be sufficiently used as a thickness for evaluating the gas permeability.

Step of Providing Permeating Gas

This step may include providing, adding or permeating a permeating gas that permeates through the set polymer unit cell. In this step, the type and molecular size of permeating gas may be adjusted depending on the purpose of measurement and evaluation. In the present invention, the constitution relating to the permeating gas is not particularly limited.

Step of Evaluating Relative Concentration

This step may include allowing or supplying the permeating gas to permeate through the polymer unit cell and evaluating the relative concentration of the permeating gas. When the permeating gas permeates through the polymer unit cell, the permeating gas may permeate only in one direction. That is, the permeating gas may flow (or be supplied) so as to permeate in a direction in which the two or more polymer unit cells are stacked.

When evaluating or measuring the permeability of the permeating gas, the method may include quantitatively evaluating or measuring the permeability expected with a change in relative concentration in a polymer unit cell in a region that first contacts a flowing permeating gas among polymer unit cells having two or more stacked layers. For example, the polymer unit cell (layer) that first contacts the permeating gas molecule may be separated from the subsequent polymer unit cell (layer), and the permeability of the first polymer unit cell that first contacts may be evaluated or measured. Otherwise, when the layer after the permeating gas passing through the first polymer unit cell standing alone is thin, the permeating gas that completely passed through the first polymer unit cell may flow back to the first polymer unit cell due to the technical characteristics of the molecular dynamics simulation, thereby doubly influencing permeability of the penetrating gas into the standalone first polymer unit cell.

Figure 9:
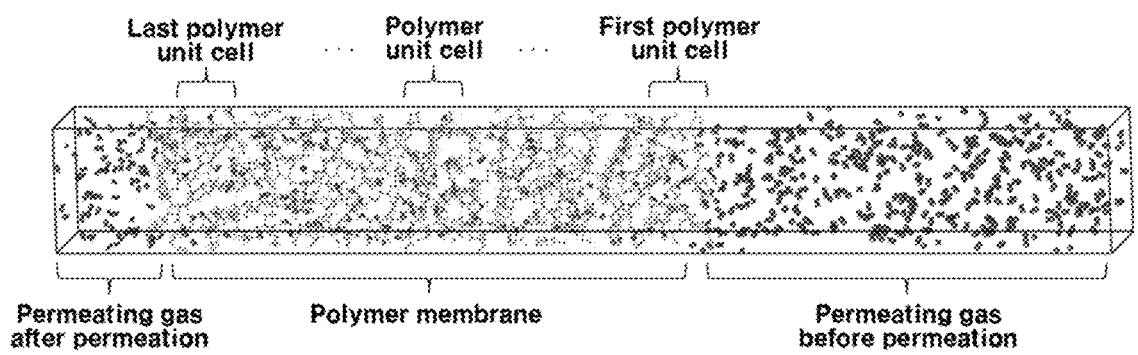
FIG. 9 is a simplified representation of the behavior of an exemplary polymer membrane and a permeating gas according to an exemplary embodiment of the present invention.
Figure 10A:
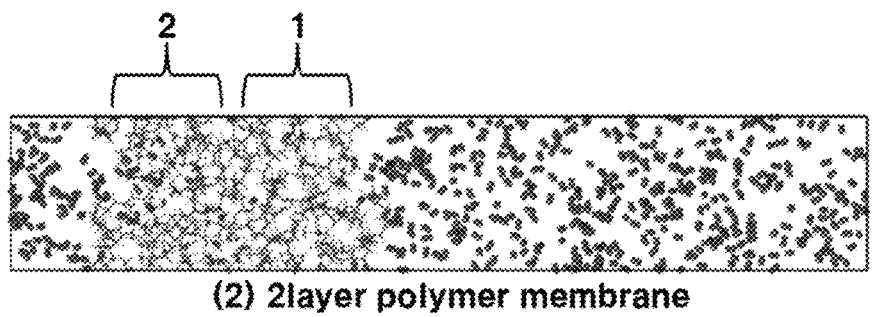
FIG. 10A illustrates polymer unit cells and permeating gases of Comparative Examples 1.
Figure 10B:
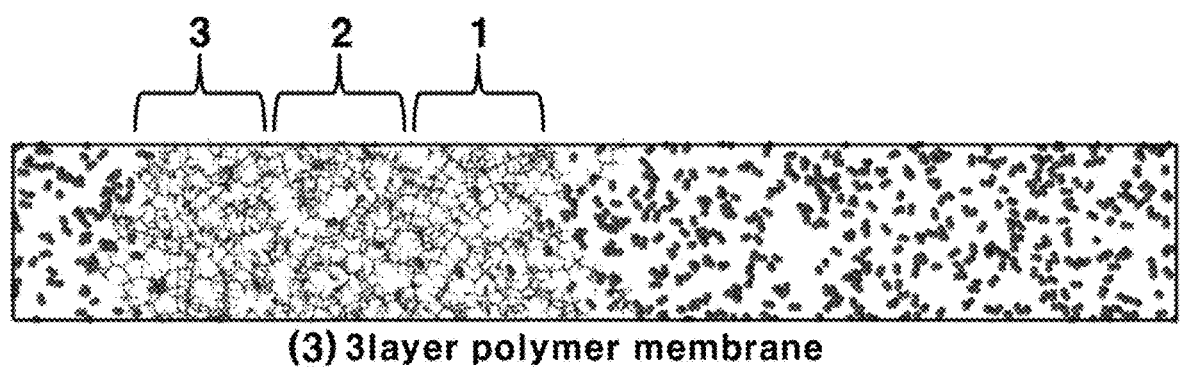
FIG. 10B illustrates polymer unit cells and permeating gases of Comparative Examples 2.
Figure 10C:
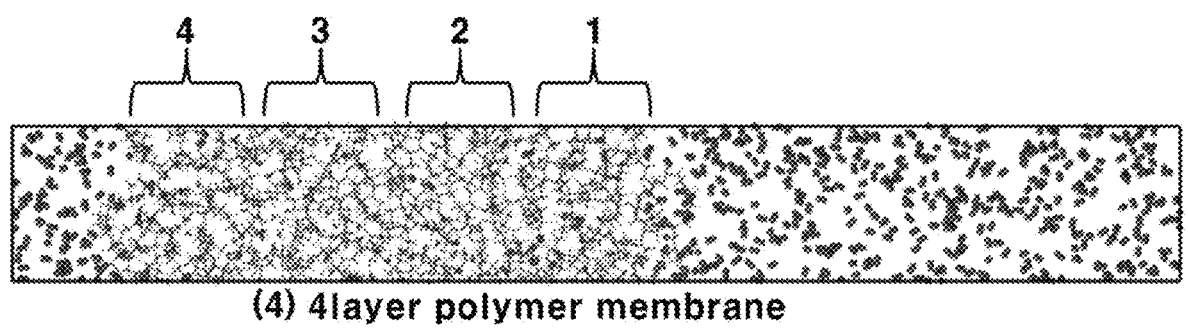
FIG. 10C illustrates polymer unit cells and permeating gases of Examples 1.
Figure 10D:
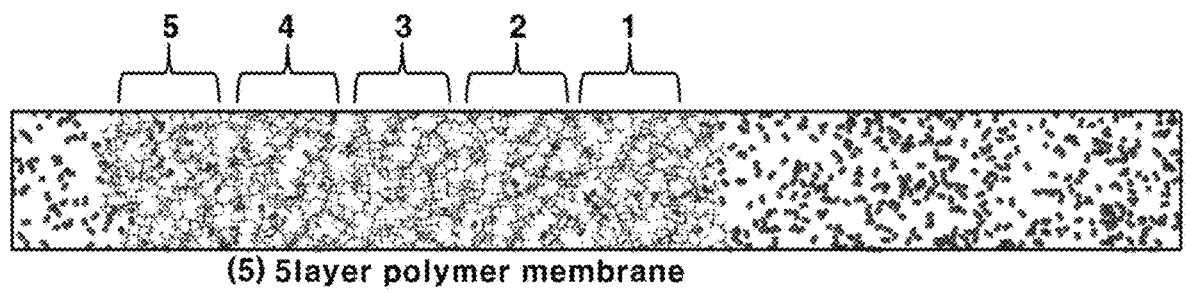
FIG. 10D illustrates polymer unit cells and permeating gases of Examples 2.

In summary, in the configuration of the molecular dynamics simulation system of the present invention, the layer may be divided into two, the polymer membrane is placed on one side, and the permeating gas is placed on the other side. When the molecular dynamics simulation is run, a behavior may occur by the interacting force between all the particles, and depending on the structure of the polymer located on the outermost surface (the surface of the polymer membrane that is in contact with the space where the permeation gas before permeation is located), permeation of the permeating gas may occur or may not occur. Particularly, the permeating gas and the polymer membrane may behave against each other due to the interacting force, and the permeating gas may permeate into the polymer membrane. FIG. 9 schematically shows the behavior of the polymer membrane and the permeating gas according to an exemplary embodiment of the present invention. As shown in FIG. 9, the polymer membrane may suitably include one or more polymer unit cells, and the permeating gas before permeation through the polymer membrane may be in contact with the first polymer unit cell.

The permeating gas before permeation, disposed on the right side of the polymer membrane in FIG. 9, may permeate into the first polymer unit cell, and this permeation may influence the quantitative evaluation of the overall permeability.

The system for measuring permeability according to an exemplary embodiment of the present invention may include a computer mainframe, a keyboard and a mouse as input devices, and a monitor as an output device.

The computer mainframe includes a central processing unit (CPU), a mass storage device (ROM, working memory, and magnetic disc), and a CD drive. Here, the mass storage unit stores a program for executing a simulation.

Hereinafter, the present invention will be described in detail with reference to examples. However, these examples are intended to illustrate the present invention, and the scope of the present invention is not limited thereto.

Comparative Example 1

As a permeating gas, hydrogen ($H_2$) was selected. The polymer chain in a polymer unit cell was set to have a main chain ($-CF_2-$) and side chains ($-OCF_2CF(CF_3)OCF_2CF_2SO_3$). At this time, the polymer chain had an equivalent weight of 1147. The main chain was hydrophobic in nature, and the side chain was hydrophilic in nature. The polymer unit cell was stacked into two layers as shown in (2) of FIG. 10, and the hydrogen gas was allowed to permeate therethrough. At this time, measurements were not taken up to a time point of 500 ps to achieve structural stabilization, and relative concentrations for 501 to 1000 ps were taken.

Comparative Example 2

Relative concentrations were taken in the same manner as described in Comparative Example 1 above, but the polymer unit cell was stacked into three layers as shown in (3) of FIG. 10.

Example 1

Relative concentrations were taken in the same manner as described in Comparative Example 1 above, but the polymer unit cell was stacked into four layers as shown in (4) of FIG. 10.

Example 2

Relative concentrations were taken in the same manner as described in Comparative Example 1 above, but the polymer unit cell was stacked into five layers as shown in (5) of FIG. 10.

Experimental Example 1: Evaluation of Optimal Number of Polymer Unit Cells

Figure 11:
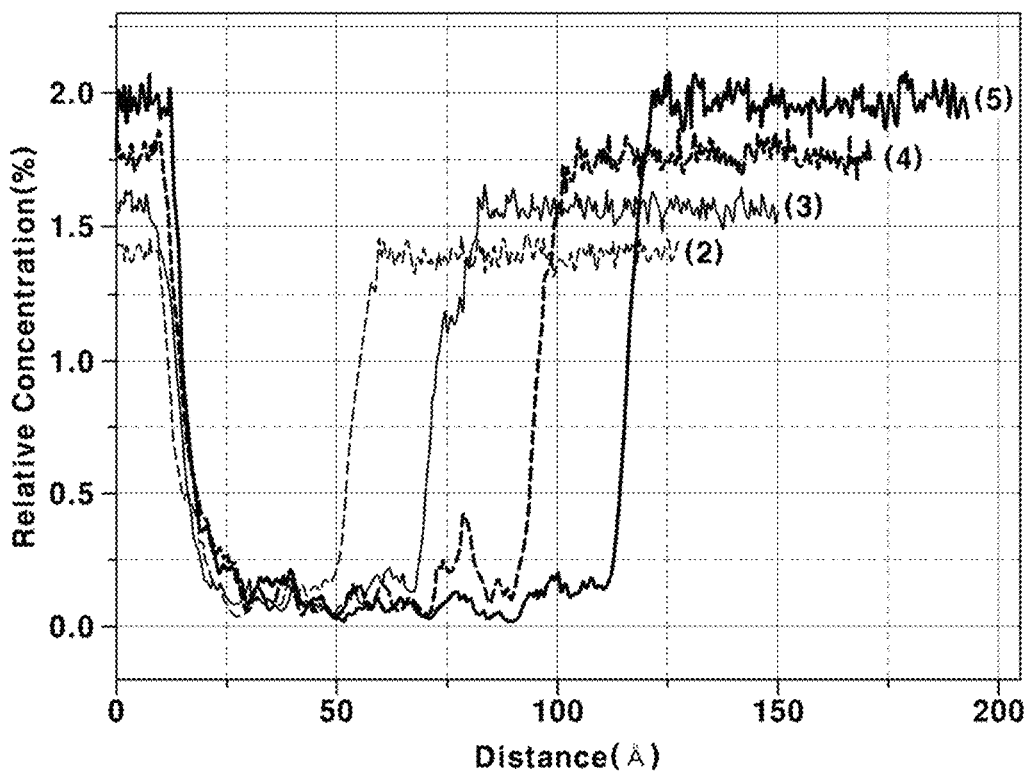
FIG. 11 is a graph showing the results of Experimental Example 1.

FIG. 11 shows the relative concentrations measured in Examples 1 and 2 and Comparative Examples 1 and 2 above. In this case, when only one polymer unit cell was applied, hydrogen gas permeated in both directions of the polymer unit cell, and the position of the polymer unit cell was changed by the pressure of the gas, making it impossible to measure the permeability for a specific time. For this reason, the application of only one polymer unit cell was excluded from the experiment.

As shown in FIG. 11, it can be seen that in the case of (2) to (5), the relative concentration decreased from the time point when the gas started to pass through the polymer unit cell to the time point when the gas passed through the polymer unit cell, and the relative concentration increased again after the gas passed through the polymer unit cell. In each of the Comparative Examples and the Examples, it can be seen that the distance at which the relative concentration decreased varied at regular intervals, and this distance maybe regarded as the polymer unit cell size.

According to various exemplary embodiments of the present invention, the permeability may be quantitatively evaluated based on the change in the relative concentration of the polymer unit cell in the region that first contacts the hydrogen gas. In the case of Comparative Example 1, it can be seen that it shows a pattern where the change at the time point when the gas passes through the polymer unit cells is somewhat irregular, and some values relatively greatly differ from a relative concentration value of 0%, indicating that the number of the polymer unit cells is not optimal. In the case of Comparative Example 2, it can be seen that the relative concentration value is closer to 0% than that in the Comparative Example 1, and the pattern is uniform, but the distance through which the permeating gas passes through the polymer unit cells is still short, and thus it is difficult to expect stable measurement. In the case of Example 1, it is shown that the pattern is partially unstable, but the distance through which the permeating gas passes through the polymer unit cells is relatively longer than that of the Comparative Examples, and thus stable measurement maybe expected. In the case of Example 2, it can be confirmed that the relative concentration value is closest to 0%, the pattern is generally uniform, and the permeation distance is long, indicating that the condition of Example 1 is optimal for the experiment.

Figure 12:
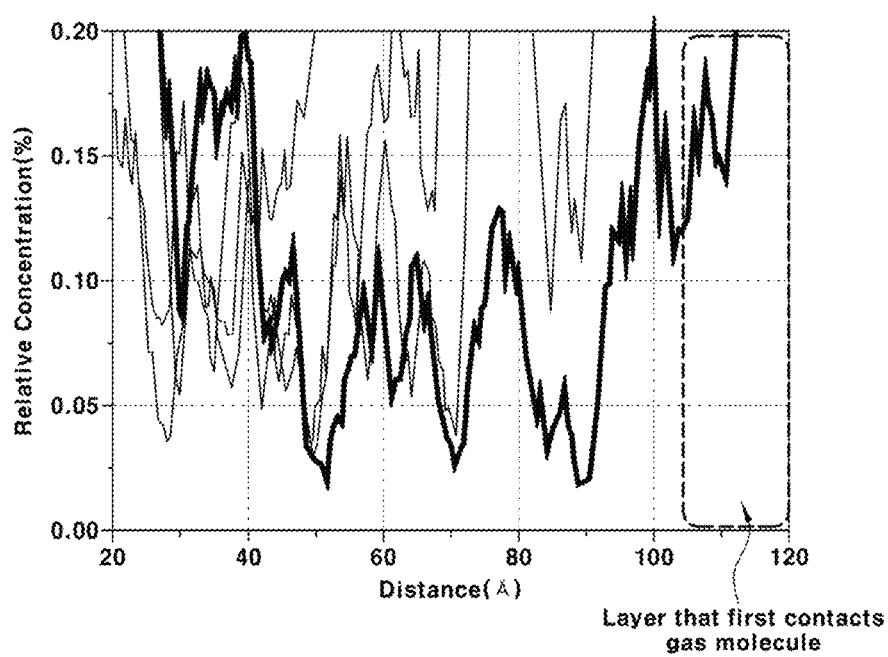
FIG. 12 is a graph showing the relative concentration of Example 2 in detail.

FIG. 12 illustrates in more detail the relative concentration behavior of Example 2 showing the most optimal number characteristic among the Examples and the Comparative Examples. As shown in FIG. 12, it can be seen that the relative concentration value in the polymer unit cell, which first contacts hydrogen gas, is different to be somewhat distinguishable from the relative concentration value in the subsequent polymer unit cell.

Experimental Example 2: Evaluation Depending on Side-Chain Structure

Figure 13:
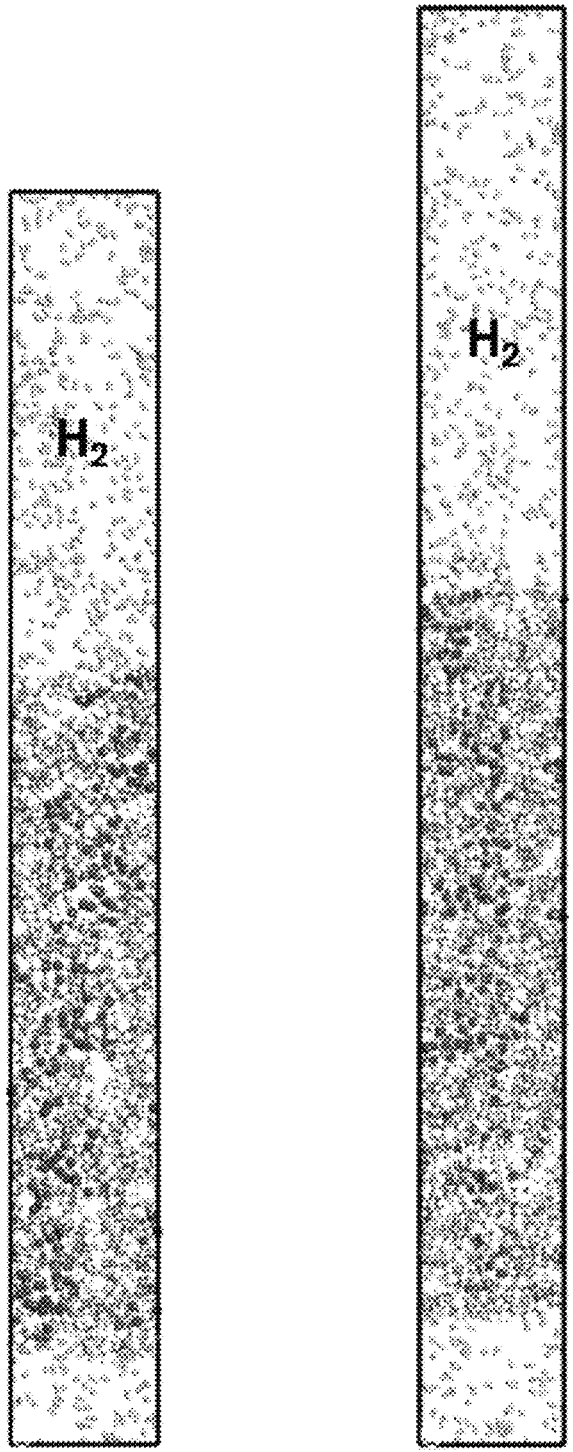
FIG. 13 shows the configuration of Experimental Example 2.

As shown in FIG. 13, a polymer unit cell (e.g., commercial polymer Nafion) including a short side chain and a polymer unit cell including a long side chain were set. For example, Formula 1 below represents the chemical structure of the side chain of the unit cell polymer of Experimental Example 2. For the polymer unit cell including the short side chain, x in Formula 1 was set at 1, and y was set at 2. For the polymer unit cell including the long side chain, x in Formula 1 was set at 1, and y was set at 8.

Figure 14:
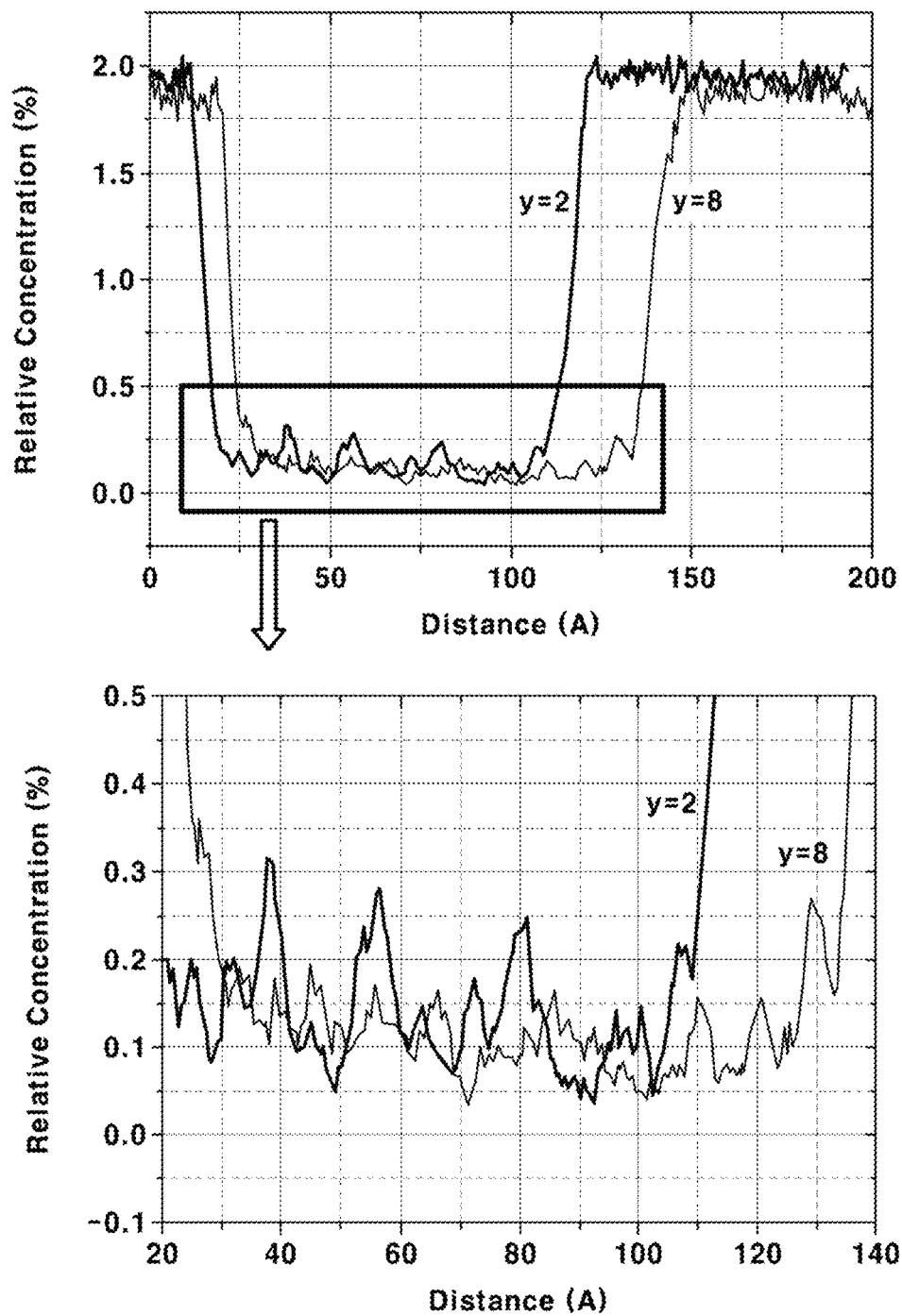
FIG. 14 is a graph showing the results of Experimental Example 2.

Formula 1:

Using hydrogen ($H_2$) gas as a permeating gas, the relative concentration for each polymer unit cell was measured, and the results of the measurement are shown in FIG. 14 and, it can be seen that the permeability of the hydrogen gas through the polymer unit cell including the short side chain is better.

As described above, according to various exemplary embodiments of the present invention, there may be provided an evaluation method for revealing the mechanism of the relationship between the molecular structure and gas permeability of a polymer membrane.

Further, according to various exemplary embodiments of the present invention, there may be provided a method which is capable of minimizing infinite influential factors that influence a gas-permeable polymer membrane, and is also capable of quantitatively evaluating the influence of gas on a single polymer chain of the polymer membrane.

The effects of the present invention are not limited to the above-mentioned effects. It should be understood that the effects of the present invention include all effects that can be inferred from the above description.

As described above, although the embodiments of the present invention have been described in detail, the claims of the present invention is not limited to the above-described embodiments, and various modifications and improvements by those skilled in the art using the basic concept of the present invention defined in the appended claims can also be included the claims of the present invention.

What is claimed is:

1. A method of measuring gas permeability of a polymer membrane, comprising:
   providing a polymer unit cell;
   adjusting a volume of the polymer unit cell;
   providing a permeating gas that permeates through the polymer unit cell; and
   supplying the permeating gas to permeate through the polymer unit cell and measuring a relative concentration of the permeating gas in the polymer unit cell,
   wherein the polymer unit cell is cubic in shape, and
   the cubic polymer unit cell comprises a single polymer chain.

2. The method of claim 1, wherein the providing the polymer unit cell comprises:
   providing a main chain of the polymer chain; and
   providing a side chain of the polymer chain.

3. The method of claim 2, wherein the providing the main chain of the polymer chain comprises adjusting a length of the main chain.

4. The method of claim 2, wherein the providing the side chain of the polymer chain comprises adjusting a length of the side chains or a number of side chains connected to the main chain.

5. The method of claim 1, wherein the polymer chain comprises a sulfonated tetrafluoroethylene based fluoropolymer-copolymer.

6. The method of claim 1, wherein the polymer unit cell further comprises a cation and water.

7. The method of claim 1, wherein the single polymer chain included in the polymer unit cell spontaneously rotates or twist to change its shape toward higher entropy.

8. The method of claim 1, wherein the single polymer chain included in the polymer unit cell changes into two or more shapes.

9. The method of claim 1, wherein, in the adjusting a volume of the polymer unit cell, the volume of the polymer unit cell is adjusted in a decreasing direction.

10. The method of claim 1, wherein, in the adjusting a volume of the polymer unit cell, a density of the single polymer chain included in the polymer unit cell is adjusted in an increasing direction.

11. The method of claim 1, wherein a number of the polymer unit cell is two or more, and the two or more polymer unit cells are stacked in one direction after the step of adjusting the volume of the polymer unit cell.

12. The method of claim 11, wherein the two or more polymer unit cells are stacked in a direction in which the permeating gas permeates through the polymer unit cells.

13. The method of claim 11, wherein the two or more polymer unit cells are stacked into at least four layers.

14. The method of claim 1, wherein, in the measuring a relative concentration of the permeating gas, the permeating gas permeates only in one direction when the permeating gas permeates through the polymer unit cell.

15. The method of claim 1, wherein, in the measuring the relative concentration of the permeating gas, a relative concentration of the permeating gas is measured in only one polymer unit cell, which first contacts the permeating gas, among the two or more stacked polymer unit cells.

* * * * *